United States Patent [19]

Hewson

[11] Patent Number: 4,960,133
[45] Date of Patent: Oct. 2, 1990

[54] ESOPHAGEAL ELECTRODE

[75] Inventor: Carl E. Hewson, Marshfield, Mass.

[73] Assignee: Brunswick Manufacturing Co., Inc., Wareham, Mass.

[21] Appl. No.: 273,928

[22] Filed: Nov. 21, 1988

[51] Int. Cl.⁵ .............................................. A61N 1/00
[52] U.S. Cl. .................... 128/784; 128/642; 128/643
[58] Field of Search .................... 128/783, 784, 419 D, 128/419 PG, 786, 642, 709, 734, 643, 642

[56] References Cited

U.S. PATENT DOCUMENTS

| | | | |
|---|---|---|---|
| 4,198,963 | 4/1980 | Barkalow et al. | 128/419 D |
| 4,351,330 | 9/1982 | Scarberry | 128/419 D |
| 4,452,254 | 6/1984 | Goldberg et al. | 128/785 |
| 4,574,807 | 3/1986 | Hewson et al. | 128/419 PG |
| 4,603,705 | 8/1986 | Speicher et al. | 128/786 |
| 4,640,298 | 2/1987 | Pless et al. | 128/784 |

Primary Examiner—Max Hindenburg
Assistant Examiner—S. Getzow
Attorney, Agent, or Firm—Wolf Greenfield & Sacks

[57] ABSTRACT

A technique has been devised to pace the heart, defibrillate the heart, or ventilate the lungs of a patient using extremely low electrical power. These techniques use an internal esophageal electrode as the basic common terminal with chest electrodes positioned to direct a particular current to a particular place depending on whether pacing, defibrillation or ventilation is to be accomplished. In accordance with the present invention a particular configuration of multiple ring electrodes has been devised to facilitate these techniques.

16 Claims, 2 Drawing Sheets

ESOPHAGEAL ELECTRODE

FIELD OF THE INVENTION

This invention relates to a particular internal electrode construction to be used with apparatus for pacing the heart, defibrillating the heart, and/or ventilating the lungs of a patient.

BACKGROUND OF THE INVENTION

When a person's heart needs to be defibrillated and converted to restore the heart beat, or when a person's heart needs to be paced to insure a rhythmic heart beat, or when a person's lungs need to be ventilated to restore breathing, sure definitive steps must be taken with rapidity, ease, and the least trauma to the patient. Methods for performing these techniques developed by applicant as sole or joint inventor are disclosed in earlier U.S. Pat. No. 4,735,206 entitled DEFIBRILLATING AND PACING THE HEART, U.S. Pat. No. 4,574,807 entitled METHOD OF APPARATUS FOR PACING THE HEART EMPLOYING EXTERNAL AND INTERNAL ELECTRODES, and U.S. Pat. No. 4,683,890 entitled METHOD AND APPARATUS FOR CONTROLLED BREATHING EMPLOYING INTERNAL AND EXTERNAL ELECTRODES. The disclosures of these earlier patents are incorporated herein by reference. All of these techniques depend on an internal esophageal electrode as the basic electrode, with other electrodes placed on the chest of the patient to establish an electrical pathway for the technique to be used. It is with this in mind that the present invention of a multiple ringed internal esophageal electrode was made.

SUMMARY OF THE INVENTION

The techniques of pacing the heart, defibrillating the heart and ventilating the lungs of a patient using an internal esophageal electrode and appropriately placed external electrodes are dependent on a specially designed internal esophageal electrode.

The internal esophageal electrode may be inserted through the mouth in the fashion of a gastric tube, or may be inserted through the nasal passages in the manner of a naso-gastric tube. This electrode will be of selected stiffness and flexibillty for such an insertion. It will be available in several diameters. In the preferred embodiment the electrode carries a plurality of circular contacts provided in the surface of the lower end of the tube. A stop may be provided on the other end of the electrode, which will engage the face of the patient so as to prevent further electrode insertion when the distal end is in the proper location. The circular rings are made in such a way as to provide the greatest possible surface area for their size and at the same time remain flexible to bending of the electrode.

The first embodiment of this invention is an esophageal electrode with multiple circular rings each one terminating in a lead, with all these leads connected together so that all the rings are electrically connected in parallel. Preferably the electrode is made in five sizes determined by the outside diameter of the polyurethane tubing which is the basic catheter on which the multiple rings are constructed to make the esophageal electrode. These sizes are 5 mm, 6 mm, 8 mm, 9 mm and 12mm in diameter. Regardless of the diameter of the basic catheter the rings are all the same. Each ring in the preferred embodiments is made of 28 closely adjacent turns of gold plated #24 copper wire (diameter 0.5 mm) which makes a ring 15 mm long. Four of these rings are provided on the tube with the distal most ring starting approximately 30 mm from the distal end, and each ring separated from the next a distance of 6 mm. These rings are flexible so as to conform to any curve the polyurethane tube assumes. The esophageal electrode may be made in other ways to achieve these dimensions and flexibility, but the construction described is preferred.

Another embodiment of this invention is an esophageal electrode with multiple circular ring contacts each terminating in a lead with all the leads connected to a selecting switch arrangement so that various contacts and combinations may be selected. In the simplest arrangement all the circular rings are connected in series and when placed in use in the patient, the most power would flow between the external electrode and the internal circular ring electrode that has the least resistance. Some power would flow from the other circular ring electrodes to the external electrode but would be much less because of the higher resistance.

In a more sophisticated use of these multiple circular ring electrodes, each of the leads terminates in an electric sensing system that measures the impedance between each circular ring electrode and the external electrode. After the system automatically measures the impedance it automatically connects the output of the defibrillator to the circular ring electrode and external electrode providing the lowest impedance to create a most precise electrical path through the heart with less power required to achieve defibrillation.

Sometimes when this invention is used, regurgitation of the stomach contents occurs. This regurgitation is life threatening if the contents of the stomach passes to the mouth and closes off the trachea preventing the patient from breathing. To prevent regurgitation, in accordance with another embodiment of this invention an inflatable cuff is placed on the esophageal electrode more proximal to the mouth than the circular ring electrodes. This cuff when inflated, after insertion of the esophageal electrode in the patient, closes off the esophagus and thereby prevents regurgitation.

In a further embodiment of this invention a number of small holes in the esophageal electrode tube in the area of the multiple rings provides a means of ensuring better contact with the esophageal wall when suction is introduced to the interior of the catheter tube. This suction keeps the esophageal interior wall tightly against the multiple rings.

BRIEF FIGURE DESCRIPTION

FIG. 1 is a perspective view of one embodiment of an esophageal electrode constructed in accordance with this invention;

FIG. IA is an enlarged fragmentary cross-sectional view of a portion of the electrode shown in FIG. 1;

DETAILED DESCRIPTION

Figure 1:
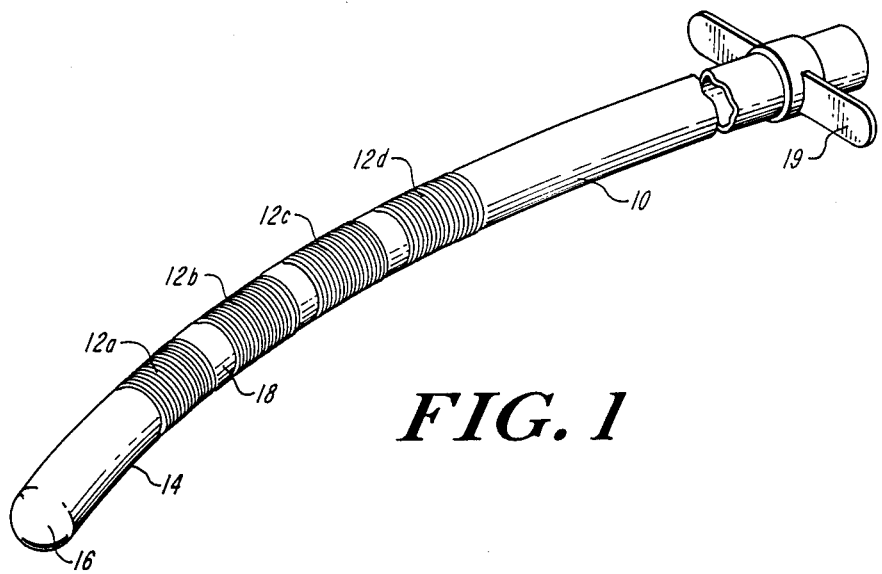

The esophageal catheter shown in FIG. 1 includes a polyurethane tube 10 preferably having an outer diameter of between 5 and 12 mm. The tube may be of a variety of lengths depending upon the size of the patient for whom it is intended. The tube must have sufficient flexibility so that it may be introduced into the esophagus either through the mouth or the nose. The tube itself may be essentially identical in construction to the conventional gastric or naso-gastric tubes widely used today.

In the preferred embodiment of FIG. 1, the tube 10 carries 4 contact rings 12a, 12b, 12c and 12d. The ring contact 12a nearest the distal end 14 of the tube 10 is spaced approximately 30 mm from that end of the tube. Preferably, each of the rings 12a through 12d are approximately 15 mm in axial extent, and the adjacent rings are separated from one another by a gap of approximately 6 mm. For ease of insertion into the esophagus, the distal end 14 of the tube is provided with a closed rounded cap 16. When the tube carrying the ring electrodes is inserted in the esophagus, the rings should be disposed in close proximity to the heart. In FIG. 1, a stop 19 is suggested which may serve to limit the depth of insertion of the tube.

It is important that the contact rings 12a to 12d not appreciably change the flexibility of the tube 10. That is, the contact rings should not introduce relatively inflexible segments to the distal end of the tube, which would interfere with insertion of the tube through the mouth or nasal passages into the esophagus. For that purpose, the contact rings 12a to 12d are each made up of continuous stands of No. 24 copper wire wound closely together. As the diameter of the No. 24 wire is approximately 0.5 mm, 28 turns are required to create a contact ring axial length of the approximately 15 mm desired.

Figure 1A:
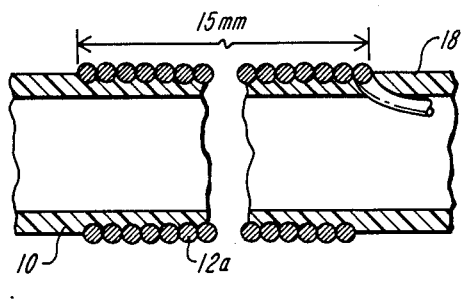

As noted in FIG. 1A, the turns of wire are wound so that the outer diameters of the turns are partially embedded in the outer surface 18 of the tube 10. The ends of the wire of each ring pass into the interior passage of the tube, and as is described below, the wires of each contact may be connected in parallel or in series depending upon the particular application for the electrode. It will also be appreciated that because the contact rings preferably engage the lining of the esophagus so as to enhance the electrical contact between them, the surfaces of the turns of wire should not lie below the plane of the surface 18 of the tube. The conductivity of the wire itself is enhanced by having the copper wire gold plated. The round wire which makes up the ring contact has several advantages. First, it is flexible so as not to interfere with the flexing of the tube. Second, it presents rounded surfaces to the interior of the esophagus so as to prevent injury. Third, the round surfaces of the wire provides maximum electrical contact surface area.

Figure 2:
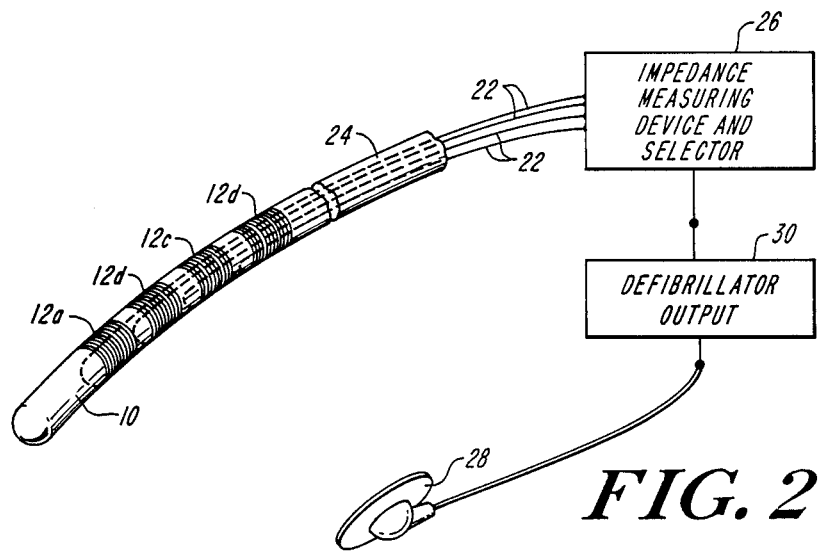
FIG. 2 is a somewhat diagrammatic view of the esophageal electrode shown in FIG. 1, but included as part of a defibrillating system.

In FIG. 2, the esophageal electrode shown in FIG. 1 is shown incorporated into a system for defibrillating the heart of a patient. This system is generally suggested in applicant's U.S. Pat. No. 4,735,206, supra. In this arrangement, the tube 10 includes the four contact rings 12a through 12d embedded in the surface of the tube, and each ring is connected to a wire conductor 22 which extends through the tube 10 and out its proximal end 24, and is connected to an impedance measuring device and selector represented by box 26. The electronics of the box 26 is well within the design capability of any skilled electronics technician in the field, and its details form no part of the present invention.

As in applicant's U.S. Pat. No. 4,735,206, the system includes an external chest electrode 28 which may be typical of those used in EKG devices, and in use is placed on the chest of the patient. The external electrode 28 and the several contact rings 12a through 12d which form four separate ring electrodes inside the body of the patient are connected across what is identified as a defibrillator output at box 30. The conductors 22 connect the rings 12 and the impedance measuring device and selector 26. The device 26 is capable of measuring the impedance between each of the separate ring contacts 12a through 12d and the exterior electrode 28. After determining which of the four paths between the ring electrodes and the external electrode has the smallest impedance, the selector places that particular ring electrode in the defibrillator circuit, and the pulse is imposed between that particular ring electrode and the external electrode 28. Because the path selected has the least impedance, the smallest pulse of energy is required to achieve defibrillation.

Figure 3:
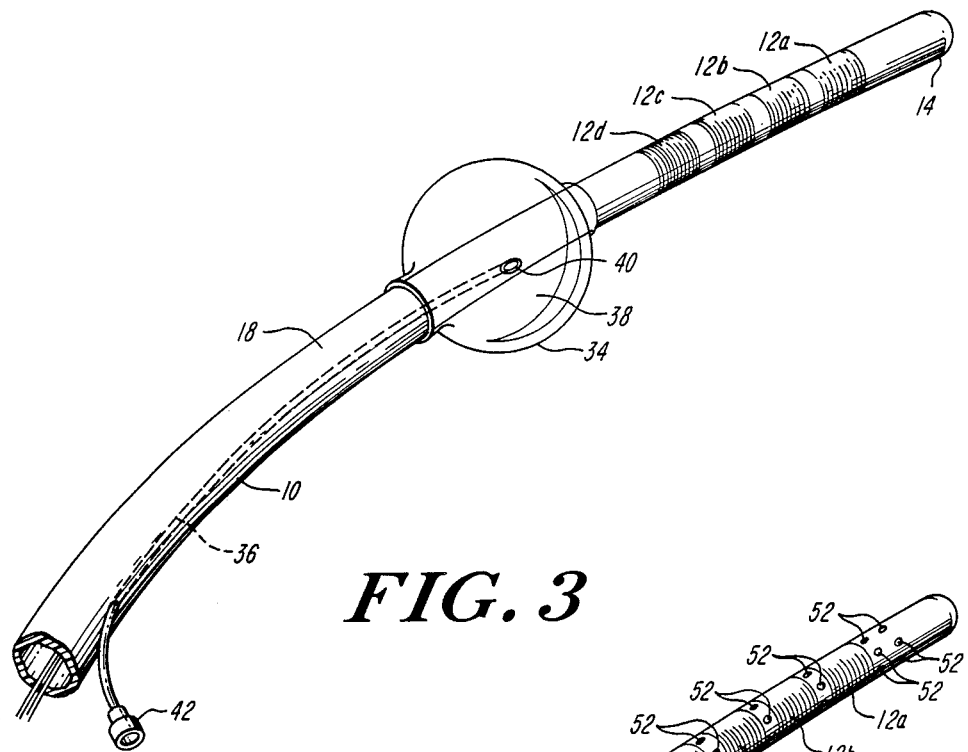
FIG. 3 is a diagrammatic view showing the esophageal electrode of this invention including an inflatable cuff.

In FIG. 3 another embodiment of esophageal electrode is shown. Like the esophageal electrode of FIG. 1, tube 10 carries preferably four ring contacts 12a through 12d spaced from one another and from the distal end 14 in the same relationship. In this embodiment, however, an inflatable cuff 34 is shown secured to the outer surface of tube 10 proximally of the ring contact 12d. The inflatable cuff 34 is made of a very soft rubber-like material well known in the catheter art, which cuff may be inflated through the lumen 36 which communicates with the interior 38 of the cuff through a port 40 in the tube 10. A check valve 42 is suggested in FIG. 3 at the proximal end of the lumen 36. When the cuff is not inflated, it lies against the outer surface 18 of the tube 10 so as not to interfere with its insertion through the mouth or nasal passages into the esophagus.

The inflatable cuff 34 is positioned on the tube 10 to seal the esophagus and prohibit the contents of the stomach which may enter the lower end of the esophagus to flow upwardly through it to the throat and mouth of the patient which may cause choking. The cuff 34 preferably lies proximally of the contact rings 12a through 12d below the carina when the tube is inserted.

Figure 4:
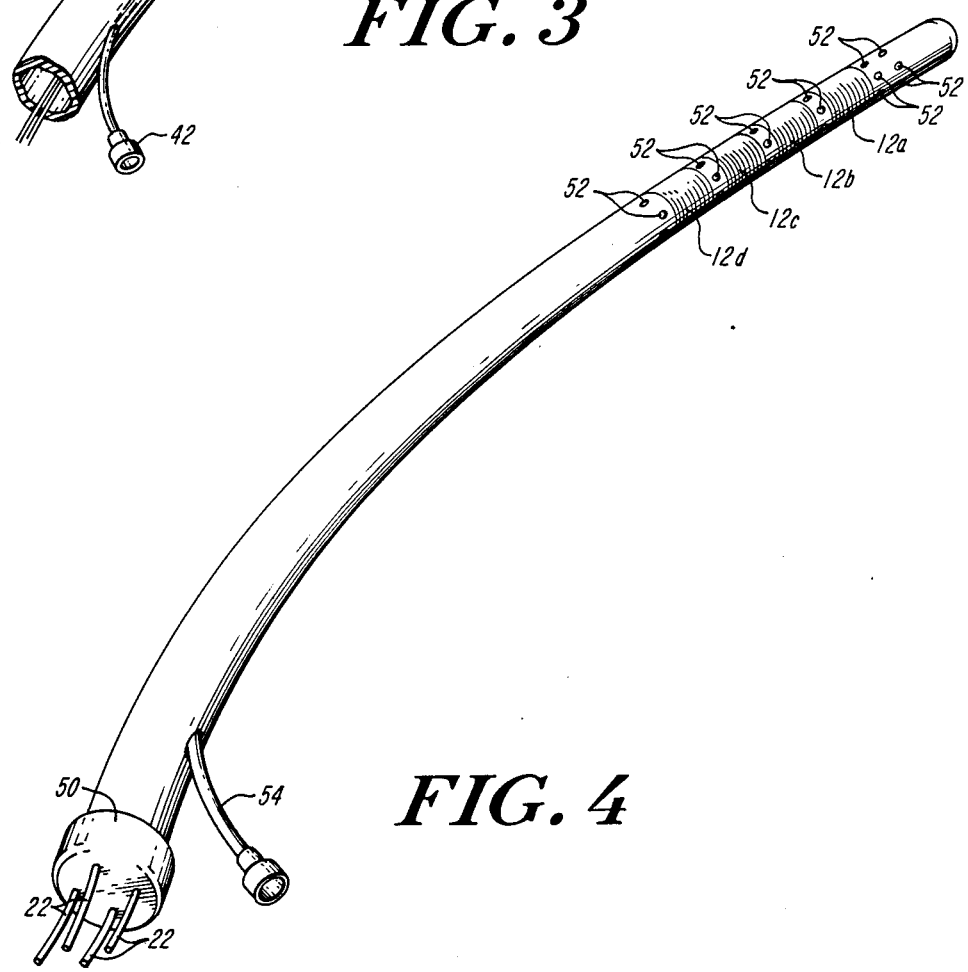
FIG. 4 is a diagrammatic view of another embodiment of esophageal electrode constructed in accordance with this invention.

In FIG. 4 yet another variation of the esophageal electrode is shown. In this embodiment also, a tube 10 is used which may be structurally identical to the tube of the embodiment shown in FIG. 1 and carries the four spaced ring contacts 12a through 12d in the same relationship to one another and the distal end of the tube as in the earlier embodiments. In this embodiment, the proximal end of the tube 10 is shown sealed by a plug 50 and the wire conductors 22 extend through the plug to the system with which the electrode is used. In this particular embodiment an array of small suction ports 52 are shown formed in the tube 10 adjacent the ring contacts 12, and the small ports 52 communicate with the interior of the tube 10. A suction coupling duct 54 is shown connected to the interior of the tube 10 at the proximal end just distally of the plug 50. The suction coupling duct 54 enables a partial vacuum to be applied to the interior of the duct, which through the suction ports 52 will draw the lining of the esophagus against the contact rings 12 so as to achieve maximum electrical contact between the esophageal lining and the contact rings. In this fashion the resistance or impedance between the contact rings and the external electrode placed on the chest for whatever purpose, will be reduced.

Having described several embodiments of the present invention, those skilled in the art will appreciate that numerous modifications may be made thereof without departing from its spirit. Therefore, it is not intended that the scope of the invention be limited to the specific embodiment illustrated and described. Rather, it is intended that the scope of this invention be determined by the appended claims and their equivalents.

I claim:

1. An esophageal electrode comprising a flexible tube sized to be inserted through the nose or mouth into the esophagus of a patient,
    and a plurality of contact rings each approximately 15 mm long embedded in the outer surface of the tube and spaced apart axially approximately 6 mm.

2. An esophageal electrode as described in claim 1 wherein
    each ring is made of a continuous strand of gold plated, copper wire.

3. An esophageal electrode as described in claim 2 wherein the wire is approximately 0.5 mm in diameter and each contact ring has approximately 28 turns of wire.

4. An esophageal electrode as described in claim 3 wherein
    said tube has distal and proximal ends, and
    an inflatable cuff is carried by the tube proximally of the contact rings.

5. An esophageal electrode as described in claim 3 wherein
    said tube has distal and proximal ends,
    a plurality of suction ports are provided in this tube,
    and means are connected adjacent the proximal end of the tube for applying a partial vacuum to the tube whereby the ports will draw the lining of the esophagus against the contact rings.

6. An esophageal electrode as described in claim 1 wherein
    each ring is made of a continuous strand of wire having approximately 28 turns.

7. An esophageal electrode as described in claim 1 wherein
    said tube has distal and proximal ends, and
    an inflatable cuff is secured to the tube proximally of the contact rings.

8. An esophageal electrode as described in claim 1 wherein
    said tube has distal and proximal ends, and
    the distal most contact ring is approximately 30 mm from the distal end of the tube.

9. An esophageal electrode as described in claim 8 wherein
    each ring is made of a continuous strand of gold plated copper wire.

10. An esophageal electrode as described in claim 9 wherein
    the wire is approximately 0.5 mm in diameter and each contact ring has approximately 28 turns of wire.

11. An esophageal electrode comprising a flexible tube sized to be inserted through the nose or mouth into the esophagus of a patient,
    and a plurality of contact rings each made of a plurality of turns of highly conductive wire on the surface of the tube so that the rings have approximately the same flexibility as the tube, wherein
    all of the contact rings are electrically connected together in parallel.

12. An esophageal electrode comprising a flexible tube sized to be inserted through the nose or mouth into the esophagus of a patient,
    and a plurality of contact rings each made of a plurality of turns of highly conductive wire on the surface of the tube so that the rings have approximately the same flexibility as the tube, wherein
    a switching device is connected to each of the contact rings enabling different rings to be selectively activated.

13. In combination with an esophageal electrode comprising a flexible tube sized to be inserted through the nose or mouth into the esophagus of a patient,
    and a plurality of contact rings each made of a plurality of turns of highly conductive wire on the surface of the tube so that the wire rings have approximately the same flexibility as the tube;
    an external electrode for placement on the chest area of the patient,
    and an electrical sensing system connected to both the contact rings and external electrode for measuring the impedance between each contact ring and the external electrode and for connecting a source of power across the contact ring and external electrode having the smallest impedance.

14. An esophageal electrode comprising a flexible tube sized to be inserted through the nose or mouth into the esophagus of a patient,
    and a plurality of contact rings each made of a continuous strand of wire and each approximately 15 mm long imbedded in the outer surface of the tube and spaced apart axially approximately 6 mm,
    wherein the wire is approximately 0.5 mm in diameter and each contact ring has approximately 28 turns of wire, and wherin
    a switching device is connected to each of the contact rings enabling different rings to be selectively activated.

15. In combination with an esophageal electrode comprising a flexible tube sized to be inserted through the nose or mouth into the esophagus of a patient,
    and a plurality of contact rings each made of a continuous strand of wire and each approximatley 15 mm long imbedded in the outer surface of the tube and spaced apart axially approximately 6 mm,
    wherein the wire is approximately 0.5 mm in diameter and each contact ring has approximately 28 turns of wire;
    an external electrode for placement on the chest area of the patient,
    an electrical sensing system connected to both the contact rings and external electrode for measuring the impedance between each contact ring and the external electrode and for connecting of a source of power across the contact ring and external electrode having the smallest impedance.

16. An esophageal electrode comprising a flexible tube sized to be inserted through the nose or mouth into the esophagus of a patient,
    and a plurality of contact rings each made of a plurality of turns of highly conductive wire on the surface of the tube so that the rings have approximately the same flexibility as the tube, wherein
    said tube has distal and proximal ends,
    a plurality of ports are provided in this tube,
    and means are connected adjacent the proximal end of the tube for applying a practical vacuum to the tube whereby the ports will draw the lining of the esophagus against the contact rings.

* * * * *